United States Patent
Kolb

(10) Patent No.: US 9,199,757 B2
(45) Date of Patent: Dec. 1, 2015

(54) DEVICE AND METHOD FOR ALIGNING CONTAINERS

(75) Inventor: Herbert Kolb, Teugn (DE)

(73) Assignee: KRONES AG, Neutraubling (DE)

( * ) Notice: Subject to any disclaimer, the term of this patent is extended or adjusted under 35 U.S.C. 154(b) by 0 days.

(21) Appl. No.: 14/343,412

(22) PCT Filed: Jul. 11, 2012

(86) PCT No.: PCT/EP2012/063584
§ 371 (c)(1),
(2), (4) Date: Mar. 31, 2014

(87) PCT Pub. No.: WO2013/045131
PCT Pub. Date: Apr. 4, 2013

(65) Prior Publication Data
US 2014/0299445 A1    Oct. 9, 2014

(30) Foreign Application Priority Data
Sep. 26, 2011   (DE) .......................... 10 2011 083 377

(51) Int. Cl.
*G01N 21/90* (2006.01)
*B65C 9/06* (2006.01)
*B65G 47/244* (2006.01)

(52) U.S. Cl.
CPC . *B65C 9/06* (2013.01); *B65C 9/067* (2013.01); *B65G 47/244* (2013.01)

(58) Field of Classification Search
CPC ....... B07C 5/122; G01N 21/90; G01N 21/972
USPC .................. 198/341.03, 375, 377.01, 377.06, 198/377.1, 410, 502.3, 575, 576, 793; 209/522, 529, 938, 939; 250/559.08
See application file for complete search history.

(56) References Cited

U.S. PATENT DOCUMENTS

| | | | | |
|---|---|---|---|---|
| 4,108,762 A | * | 8/1978 | Babunovic et al. | 209/524 |
| 4,776,466 A | * | 10/1988 | Yoshida | 209/565 |
| 4,832,173 A | * | 5/1989 | Hattori et al. | 198/377.1 |
| 5,249,034 A | * | 9/1993 | Minato | 356/606 |
| 5,405,015 A | * | 4/1995 | Bhatia et al. | 209/524 |
| 5,510,610 A | * | 4/1996 | Baldwin | 250/223 B |
| 6,298,974 B1 | * | 10/2001 | Heuft et al. | 198/339.1 |

(Continued)

FOREIGN PATENT DOCUMENTS

| | | |
|---|---|---|
| DE | 102005041497 A1 | 3/2007 |
| DE | 102005050902 A1 | 5/2007 |

(Continued)

OTHER PUBLICATIONS

International Search Report, PCT/EP2012/063584, Oct. 16, 2012.

*Primary Examiner* — Douglas Hess
(74) *Attorney, Agent, or Firm* — Marshall, Gerstein & Borun LLP

(57) ABSTRACT

A device and a method for aligning containers including an evaluation unit, which is capable of determining the position and/or the rotary position of at least one feature of the surface of containers to be aligned, by calculating image data of said feature in at least two views that differ with respect to the imaged rotary position of the containers, and where picture distortions and contrast limitations caused by the perspective can be compensated. The reliability of rotary position recognition and correction can thus be improved when aligning the containers.

17 Claims, 1 Drawing Sheet

(56) References Cited

U.S. PATENT DOCUMENTS

| | | | |
|---|---|---|---|
| 6,452,156 B2 * | 9/2002 | Lindner | 250/223 B |
| 6,483,935 B1 * | 11/2002 | Rostami et al. | 382/141 |
| 6,868,652 B2 * | 3/2005 | Arends et al. | 53/446 |
| 7,013,624 B2 * | 3/2006 | Zwilling | 53/544 |
| 7,414,716 B2 * | 8/2008 | Sones et al. | 356/239.4 |
| 7,816,639 B2 * | 10/2010 | Diehr et al. | 250/223 B |
| 8,373,756 B2 * | 2/2013 | Lindner | 348/161 |
| 8,424,276 B2 * | 4/2013 | Krause | 53/544 |

FOREIGN PATENT DOCUMENTS

| | | |
|---|---|---|
| DE | 102009020919 A1 | 11/2010 |
| EP | 0491555 A1 | 6/1992 |
| WO | WO-2008072070 A2 | 6/2008 |
| WO | WO-2009072157 A1 | 6/2009 |

* cited by examiner

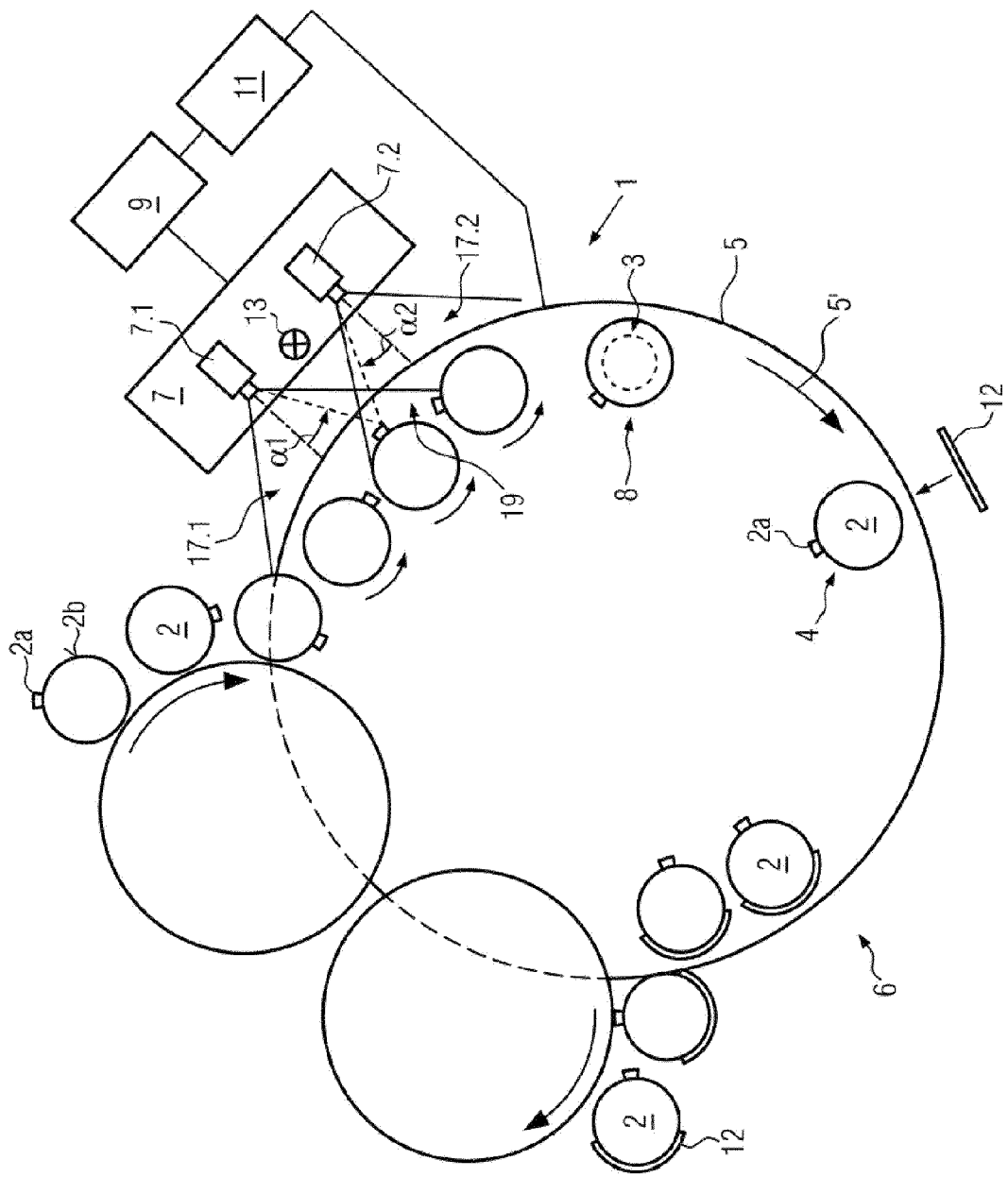

DEVICE AND METHOD FOR ALIGNING CONTAINERS

CROSS-REFERENCE TO RELATED APPLICATION

The present application is the United States national phase of International Patent Application No. PCT/EP2012/063584, filed Jul. 11, 2012, which application claims to German Application No. DE 10 2011 083 377.3 filed Sep. 26, 2011. The priority application is hereby incorporated by reference.

FIELD OF THE DISCLOSURE

The present disclosure relates to a device for aligning containers, a corresponding method for aligning containers, a labeling machine and a labeling method.

BACKGROUND

Before containers, such as beverage bottles, are labeled, they are normally moved to an appropriate target rotary position with respect to the labeling device in question. To this end, it is known e.g. from DE 10 2005 050 902 A1 and DE 10 2009 020 919 A1 to conduct the containers, while they are rotating about their main axis, past a camera system so as to image the whole circumference of the containers in a plurality of camera pictures for identifying a feature on the container surface, e.g. a molding seam. The actual rotary position of the container is ascertained on the basis of the identified feature and the container is moved to a target rotary position as a starting point for labeling.

This, however, entails the following problems:

1. In the case of comparatively small features, such as a molding seam on the surface of the container, the contours of the feature will only cause comparatively weak differences in contrast in the reflected incident light. This may perhaps not suffice for allowing an exact determination of the position of the feature, in particular when an only weakly contoured feature is seen in a view that is substantially a front view. Hence, the actual rotary position of the container cannot be determined, or only be determined with insufficient accuracy on the basis of said feature.

2. Contours of elevated features are shown with different contrast differences and/or edge widths at different rotary positions, i.e. at different object angles. Also this may have the effect that the position and/or the rotary position of a relief-like feature on the container surface can be determined only with insufficient accuracy or reliability.

3. In the areas of the features to be identified, the diameter of the container may exhibit certain tolerances, which result from the manufacturing process and which are relevant to position determination. Depending on the dimensional accuracy of the container to be examined, this may lead to an object angle-dependent inaccuracy in the determination of the position or rotary position of the identified feature. Therefore, it may be impossible to calculate a correct correction angle for moving the container to a target rotary position for subsequent labeling.

As suggested in DE 10 2005 050 902 A1, the last mentioned problem can be solved by aligning the containers in successive inspection units with increasing accuracy. In addition to the considerable complexity of equipment and the large amount of time required, the problems specified under 1 and 2 can, however, not be solved or may even be aggravated by this course of action.

Hence, there is a need for devices and methods for aligning containers, in particular for a subsequent labeling of containers, which have been improved in this respect.

SUMMARY OF THE DISCLOSURE

The posed task is solved by the present disclosure via a device for aligning containers an evaluation unit is provided, which is capable of determining the position and/or the rotary position of at least one feature of the surface of the container to be aligned, by mutually calculating image data of the feature in at least two views, which differ with respect to the respective imaged rotary position of the containers.

It is thus possible to confirm and/or correct e.g. the position and/or the rotary position of a feature, which cannot be discerned with sufficient reliability in a single view, on the basis of a second view. Likewise, object angle-dependent distortions and/or differences in contrast of characteristic relief-like structures in at least two corresponding image areas of the at least two views can be compared to one another and/or used for mutual calculation. This allows the corresponding image data to be e.g. averaged, subtracted or added and the like. In particular, an interpolation of image data from the at least two different views of the container surface is possible.

In other words, relief-like features are imaged from different angles of view for obtaining from the different views information on the extent to which the differences in contrast and edge widths of specific contours depend on the object angle. On the basis of this information, a corrected image can be produced for image evaluation and position determination. A particularly advantageous method of producing corrected images is the interpolation of different views, e.g. the bilinear interpolation, the bicubic interpolation, the nearest-neighbor interpolation or the Lanczos interpolation.

Preferably, the cameras are arranged such that object angles of corresponding areas of the feature differ from one another in at least two views by at least 30°, in particular by at least 45°. The object angle is here, by definition, the angle of the object relative to the optical axis of the objective of the camera, i.e. a measure for the line of sight or viewing direction of the objective of the camera with respect to the object to be measured. Areas of the feature corresponding to one another are here e.g. characteristic edges and other characteristic raised and/or recessed portions. In the case of the above-mentioned object angle differences, relief-like structures will create, with a comparatively high probability, different shadows, reflections and the like in the pictures taken by the cameras. Thus, at least two different image data sets, which can be compared to one another and/or used for mutual calculation, are obtained for individual features.

According to a particularly advantageous embodiment of the device according to the present disclosure, the evaluation unit is configured such that it is capable of creating from the image data of the at least two views a virtual view of the container. An idealized image of the container with reduced image defects can be calculated in this way. This allows the position and/or the rotary position of features on the surface of the container to be determined with higher accuracy and reliability. Also a plurality of virtual views may here be combined so as to obtain a panorama view of the container.

Preferably, the cameras have at least one image area overlapping along the conveying path, so as to image the feature in the overlapping image area under different object angles. This allows the container to be imaged in the overlapping image area with a plurality of cameras simultaneously so as to obtain image data sets that can be used for mutual calculation in the way specified in the present disclosure. The machine angle required for rotary position determination and container orientation can thus be reduced.

Preferably, a plurality of overlapping image areas is provided along the conveying path, so as to image the container in the overlapping image areas in a full-circumference imaging mode. It is thus possible to carry out a full-circumference identification of suitable features on the surface of the container and a determination of an actual rotary position of the container on the basis of a comparison of several views under different object angles in a single inspection and alignment unit. In particular, a multi-step sequential alignment with separate camera systems, which is known from the prior art, is thus rendered superfluous.

A particularly advantageous embodiment of the device according to the present disclosure additionally comprises an illumination unit, especially a directional illumination unit, for illuminating the containers, said illumination unit being directed such that it is able to create different shadows and/or reflection patterns at the features in said at least two views. Also low-contrast features, such as e.g. structures which are only slightly raised and/or recessed, e.g. molding seams, can thus be identified and localized with increased reliability.

Preferably, the device according to the present disclosure comprises a control unit for aligning the rotary position of the container on the basis of the determined position and/or determined rotary position of the feature. And actual rotary position of the container, which has been determined according to the present disclosure with increased accuracy and reliability, can thus be used directly as an initial value for a subsequent correction of the rotary position. In particular, an immediately following labeling step can be carried out on the basis of the corrected rotary position of the container.

The posed task is also solved by a labeling machine including the device for aligning containers according to the present disclosure. Since labels should normally not be applied to raised or recessed areas of containers, the device for aligning containers according to the present disclosure can be used in a particularly advantageous manner prior to an immediately following labeling step.

The posed task is also solved by a method including the steps of a) conveying and rotating the containers; b) imaging the containers from at least two different camera positions so as to image a circumferential area of each of the containers in at least two views; and c) determining the position and/or rotary position of at least one feature of the surface of the container by mutually calculating image data of the feature in the at least two views.

Due to the fact that characteristic features are imaged in different views, the features represented in said different views with respective different contrasts and/or edge widths can be compared to one another and/or mutually calculated. It is thus e.g. possible to avoid a feature from not being identifiable, or from being only identifiable with insufficient contrast, i.e. with insufficient reliability, in a specific view. The plausibility of individual measurements can be examined as well.

Preferably, image data of the at least two views are interpolated and/or added in step c). This allows e.g. image defects of individual views to be averaged and/or corrected in a weighted manner. For example, depending on the quality of the respective feature to be identified in a specific view, an interpolation can be calculated preferentially on the basis of a qualitatively preferred view.

In accordance with a particularly advantageous embodiment of the method according to the present disclosure, a virtual view of the container is created from the image data of the at least two views in step c). A view that is particularly advantageous for evaluating the position of the feature can be calculated in this way. The term view describes here a transformation into an angle of view that is advantageous for further processing of the image data. Since the camera positions and the object position of the container during taking of a picture can be assumed to be known, also several virtual views can be calculated, compared and/or combined.

Preferably, the at least two views of the feature include an overlapping image area and are imaged substantially simultaneously. This allows the at least two views to be imaged within the overlapping image areas in a particularly time- and space-saving manner. Measurement errors can be reduced still further by simultaneously imaging the containers.

A particularly advantageous embodiment of the method according to the present disclosure additionally comprises a step d) of determining an actual rotary position of the containers on the basis of the position and/or rotary position of the least one feature determined in step c), and of ascertaining a rotary position correction for moving the container to a target rotary position. The error of the accessed target rotary position can be minimized in this way.

Preferably, the method according to the present disclosure additionally comprises a step e) of moving the container to the target rotary position. The method according to the present disclosure can thus be used in a particularly efficient manner for a labeling step following immediately afterwards.

The posed task is additionally solved by a labeling method comprising the method for aligning containers according to the present disclosure as well as a step of labeling the containers, wherein the accessed target rotary position is a starting position and/or reference position for labeling. This allows a particularly space-saving and precise labeling operation while avoiding an application of labels to regions with raised and/or recessed surface areas.

BRIEF DESCRIPTION OF THE DRAWING

A preferred embodiment of the disclosure is shown in the drawing which shows a schematic top view.

DETAILED DESCRIPTION

As can be seen from the only FIGURE, which shows a schematic top view, a preferred embodiment of the device 1 for aligning containers 2, such as beverage bottles or the like, according to the present disclosure comprises a plurality of rotatable holders 3 for receiving, holding and aligning the containers 2 so as to bring them into a target rotary position 4 for a subsequent processing step, in particular for labeling the containers 2. The holders 3 comprise e.g. turntables or the like, which are concealed in the FIGURE by the respective containers 2. The containers 2 move along a conveying path 5, which may e.g. be a constituent part of a carousel-like labeler 6, along a camera system 7 oriented substantially tangentially to the conveying path 5. In the course of this movement, the containers 2 are rotated about their main axis and imaged, preferably in a full-circumference imaging mode, at different rotary positions. The respective actual rotary positions 8 of the containers 2 can be calculated from image data of the camera system 7 by means of an evaluation unit 9, and also individual correction angles for moving the containers 2 to the target rotary position 4, which is identical for all containers 2, can be calculated in this way. In the FIGURE, only individual container positions, which make the disclosure more easily understandable, are indicated along the conveying path 5.

The camera system 7 comprises at least two cameras 7.1 and 7.2, which are arranged along the conveying path 5, i.e. in succession with respect to the conveying direction of the containers 2 symbolized by an arrow 5'. In addition to the evaluation unit 9 for processing image data of the cameras 7.1 and 7.2, a control unit 11 is provided for accurately rotating the individual holders 3 from the respective actual rotary position 8 into the target rotary position 4. Different rotary positions of the containers can be discerned in the FIGURE, e.g. on the basis of a characteristic relief-like feature 2a provided on the container surface 2b, e.g. in the form of a molding seam.

The mode of operation of the camera system 7 and f the evaluation unit 9 is exemplarily described only on the basis of the two depicted cameras 7.1 and 7.2. However, the camera system 7 preferably comprises additional cameras, respective neighboring cameras cooperating then in the same way as described herein below for the two cameras 7.1 and 7.2.

The relief-like structured features 2a may comprise raised as well as recessed portions. The device 1 according to the present disclosure particularly aims at reliably detecting characteristic contours, edges and the like of the features 2a and localizing them on the basis of the image data of the cameras 7.1, 7.2 so as to determine the actual rotary position 8 with respect to the conveying path 5 from the position data of the features 2a. For subsequent labeling of the containers 2 with labels 12, said labeling being exemplarily indicated in the FIGURE, the containers 2 have to be moved to the predetermined target rotary position 4, which is preferably a starting position for labeling the containers 2.

In the area of the camera system 7 an illumination unit 13 is provided, e.g. a row of light emitting diodes or the like. The illumination unit 13 produces on the containers 2 a characteristic reflex, e.g. a bright strip, which is imaged by the cameras 7.1 and 7.2 at different object angles with respect to the respective center axis of the object. The radiation characteristics of the illumination unit 13 are of such a nature that, depending on the object angle $\alpha_1, \alpha_2$ of the structure in question, different contrast formations in the form of reflections and/or shadows are created on the features 2a, in particular on edges, contours and the like. Hence, one and the same surface structure, here exemplarily the feature 2a, is imaged in the camera pictures of the cameras 7.1 and 7.2 with different brightness profiles, edge widths, perspective distortions and the like. In other words, the containers 2 are seen by the cameras 7.1 and 7.2 at different rotary positions and one and the same feature 2a is imaged at different object angles $\alpha_1, \alpha_2$ in at least two camera pictures.

Depending on the relative position and the orientation of the features 2a with respect to the cameras 7.1 and 7.2 as well as of the illumination unit 13, different image data of one and the same feature 2a are thus created by the cameras 7.1 and 7.2. The corresponding views of the container surface 2b and of the features 2a are preferably simultaneously recorded by the cameras 7.1 and 7.2. This facilitates the synchronization and the temporal classification of the individual camera pictures and the assigning of position data, such as world coordinates of the container surface, to the image data of the cameras 7.1 and 7.2. It is, however, not absolutely necessary to trigger, i.e. activate, the cameras 7.1 and 7.2 in common.

The image areas 17.1 and 17.2 of the cameras 7.1 and 7.2, which are symbolically indicated by the respective peripheral rays, overlap in an overlapping area 19 in the conveying direction of the containers 2. The feature 2a of the container surface 2b is imaged by the cameras 7.1 and 7.2 preferably as long as said feature 2a is located in the overlapping image area 19. The overlapping area 19 is, however, not absolutely necessary. In view of the fact that the position of the containers 2 along the conveying path 5 as well as the rotary positions of the associated holders 3 are known, e.g. by means of suitable incremental encoders, imaging of the container 2 could take place at arbitrary moments in time as long as it is guaranteed that a specific feature 2a on the container surface 2b is imaged by at least two cameras 7.1 and 7.2 under different object angles $\alpha_1, \alpha_2$. In other words, arbitrary combinations of such different views of the feature 2a are imaginable. Preferably, full-circumference imaging of the container 2 under different object angles is guaranteed.

In order to obtain views with sufficiently different contrast effects of the features 2a, the cameras 7.1 and 7.2 should be provided at a sufficient distance from one another, measured along the conveying path 5. This guarantees that the difference between the object angles $\alpha_1, \alpha_2$ of the cameras 7.1, 7.2 will be sufficiently large. Preferably, the difference between the object angles $\alpha_1$ and $\alpha_2$, which are enclosed with the respective optical axis of the cameras 7.1 and 7.2 when seen in a top view, amounts to at least 30°, in particular at least 45°. In the example shown, the object angles $\alpha_1, \alpha_2$ have different signs so that, in the case of difference formation, the values of the object angles $\alpha_1, \alpha_2$ are added together.

The different views of the containers 2 recorded by the cameras 7.1 and 7.2 are combined by the evaluation unit 9 so as to obtain preferably a virtual view of the container 2. The basis for such a conversion may e.g. be an interpolation, a difference formation or a summation of individual views of the cameras 7.1 and 7.2. Suitable methods comprise e.g. a bilinear or bicubic interpolation or an interpolation according to the nearest-neighbor method. Imaging-dependent distortions occurring in the case of large object angles can be compensated and insufficient contrast differences at raised or recessed structures, which primarily occur in the case of comparatively small object angles, can be avoided in at least one imaged view of the feature 2a. The different camera pictures of feature 2a may also be utilized for improving the reliability of feature identification in the sense of a plausibility check.

Different perspective distortions of contours can be compensated at least partially by interpolation of individual views of the feature 2a. The accuracy of position determination of characteristic edges and the like on raised or recessed structures can be improved in this way. In this context it is, for example, also possible to create by interpolation a virtual view of the container surface 2b, which is optimized with respect to an improved discernability and localization of the feature 2a.

Tolerances of the container dimensions can be taken into account by comparing positions and or rotary positions of the feature 2a in the individual views of the cameras 7.1 and 7.2 with value tables or the like. For example, in the case of given dimensions of a container, only specific positions of features 2a on an e.g. cylindrical container surface 2b are possible. By means of a comparison with value tables, it can therefore be determined whether pairs or groups of values ascertained from different views of the feature 2a, which belong together, correspond with a value table of a specific given container diameter or the like.

The device 1 according to the present disclosure can e.g. be used for imaging a continuous flow of containers 2, which are to be aligned and labeled, under different object angles $\alpha_1$ and $\alpha_2$ by means of at least two cameras 7.1 and 7.2 so as to determine from the corresponding images a position of a feature 2a with increased accuracy. To this end, the containers 2 are, preferably continuously, moved along the conveying path 5 past the camera system while the containers 2 rotate continuously about their main axis. Preferably, a sufficiently large number of pictures of the containers 2 is then taken for imaging at least the whole circumference of the containers in the pictures. It is thus guaranteed that, even in the case of a random distribution of the original rotary positions of the containers, the feature 2a will be imaged in at least two pictures of the container 2 according to the present disclosure.

In this context it is presupposed that the triggering of individual camera pictures of the cameras 7.1 and 7.2 is synchronized with the transport of the container 2 along the conveying path 5 as well as with the rotary movement of the associated holder 3. This can be guaranteed in the manner known by servomotors and the like. In addition, a synchronization of the image coordinates in the individual camera pictures with the world coordinates of the containers 2 and the cameras 7.1 and 7.2 is guaranteed, e.g. in the manner known with reference bodies, by learning evaluation algorithms and/or taking into account the intrinsic camera parameters. To this end, standard photogrammetric methods can be used.

The disclosure has been described on the basis of an individual feature 2a on the container surface 2b making use of only two cameras 7.1, 7.2 whose image areas 17.1 and 17.2 provide in a common overlapping area 19 different views of features 2a to be identified. An arbitrary number of features 2a may, however, the examined within an overlapping area 19. Likewise, a plurality of overlapping areas 19 may be arranged in succession in the conveying direction of the containers 2. In this case, a corresponding number of cameras would have to be provided.

On the basis of at least one identified feature 2a, an actual rotary position 8 of the containers 2 with respect to the conveying path 5 and/or with respect to a subsequent labeling unit is calculated. The calculated actual rotary position 8 is preferably corrected immediately afterwards by calculating a difference from a predetermined target rotary position 4, in particular for labeling, and by moving the container 2 to the target rotary position 4. The target rotary position 4 is then preferably used as a starting position and/or as a reference position for a labeling step carried out immediately afterwards. Intermediate steps, such as a more precise orientation of the containers 2 prior to labeling, can thus be dispensed with. The device 1 for aligning containers according to the present disclosure can thus be integrated in a labeling machine 6 in a particularly advantageous manner.

What is claimed is:

1. A device for aligning containers, comprising:
    rotatable holders for holding and individually rotating the containers;
    at least two cameras provided along a conveying path for the containers for imaging the containers in a plurality of views differing from one another with respect to the imaged rotary position of the containers, thereby imaging at least one feature of the containers at different object angles and creating different image data of the feature by the cameras;
    an evaluation unit for determining the position of the features on the surface of the containers on the basis of these views, and
    the evaluation unit being configured to be capable of determining at least one of the position or the rotary position of the feature of the surface of the container by at least one of mutually calculating and comparing the different image data of the feature in at least two of the views.

2. The device according to claim 1, the cameras being arranged such that object angles ($\alpha1$, $\alpha2$) of areas of the feature, which correspond to one another in the at least two views, differ from one another by at least 30°.

3. The device according to claim 2, and the object angles differing from one another by at least 45°.

4. The device according to claim 1, and the evaluation unit being configured to be capable of creating from the image data of the at least two views a virtual view of the container.

5. The device according to claim 1, and the cameras have at least one image area overlapping along the conveying path, so as to image the feature in the overlapping image area under different object angles ($\alpha1$, $\alpha2$).

6. The device according to claim 5, and a plurality of overlapping image areas is provided along the conveying path, so as to image the container in the overlapping image areas in a full-circumference imaging mode.

7. The device according to claim 1, further comprising an illumination unit for illuminating the containers to create different shadows and/or reflection patterns at the feature in said at least two views.

8. The device according to claim 7, the illumination unit comprising a direction illumination unit.

9. The device according claim 1, further comprising a control unit for aligning the rotary position of the containers on the basis of the determined position and/or determined rotary position of said feature.

10. A labeling machine including the device according to claim 1.

11. A method of aligning containers, comprising:
    a) conveying and rotating the containers;
    b) imaging the containers from at least two different camera positions so as to image a circumferential area of each of the containers in at least two views differing with respect to the imaged rotary position of the respective container thereby imaging at least one feature of the containers at different object angles and creating different image data of the feature; and
    c) determining the position and/or the rotary position of the feature of the surface of the container by at least one of mutually calculating and comparing the different image data of the feature in the at least two views.

12. The method according to claim 11, the image data of the at least two views being interpolated and/or added in step c).

13. The method according to claim 11, and creating a virtual view of the container from the image data of the at least two views in step c).

14. The method according to claim 11, the at least two views including an overlapping image area and being imaged substantially simultaneously.

15. The method according to claim 11, further comprising determining an actual rotary position of the containers on the basis of the position and/or rotary position of the least one feature determined in step c), and of ascertaining a rotary position correction for moving the container to a target rotary position.

16. The method according to claim 15, further comprising moving the container to the target rotary position.

17. The method according to claim 16, and labeling the containers where the accessed target rotary position comprises a starting position and/or reference position for labeling.

* * * * *